US008975083B2

(12) United States Patent
Selby et al.

(10) Patent No.: US 8,975,083 B2
(45) Date of Patent: Mar. 10, 2015

(54) OIL LIFE MEASUREMENT

(71) Applicants: Theodore W. Selby, Midland, MI (US);
Gregory C. Miiller, Rhodes, MI (US)

(72) Inventors: Theodore W. Selby, Midland, MI (US);
Gregory C. Miiller, Rhodes, MI (US)

(73) Assignee: Tannas Company, Midland, MI (US)

( * ) Notice: Subject to any disclaimer, the term of this patent is extended or adjusted under 35 U.S.C. 154(b) by 0 days.

(21) Appl. No.: 13/998,187

(22) Filed: Oct. 9, 2013

(65) Prior Publication Data

US 2014/0099728 A1    Apr. 10, 2014

Related U.S. Application Data

(60) Provisional application No. 61/795,088, filed on Oct. 10, 2012.

(51) Int. Cl.
*G01N 33/28* (2006.01)
*G01N 25/26* (2006.01)

(52) U.S. Cl.
CPC ............ *G01N 25/26* (2013.01); *G01N 33/2888* (2013.01); *G01N 33/2805* (2013.01)
USPC ............................... 436/147; 436/60; 422/51

(58) Field of Classification Search
CPC ....... G01N 25/20; G01N 25/22; G01N 25/26; G01N 33/26; G01N 33/28; G01N 33/2805; G01N 33/2888
USPC ................ 436/60, 147, 180, 183; 422/50, 51, 422/82.12, 501, 537, 546, 560, 561
See application file for complete search history.

(56) References Cited

U.S. PATENT DOCUMENTS 7,678,328 B1    3/2010    Secrist et al.

OTHER PUBLICATIONS

ASTM International, ASTM D2272-09, "Standard Test Method for Oxidation Stability of Steam Turbine Oils by Rotating Pressure Vessel," Sep. 2009.
Selby, Theodore W., E-mail of Feb. 16, 2011 10:14 AM, "Selby Presentation at OilDoc Conf.final.ppt/Quantum status," printed Feb. 16, 2011.
Selby, Theodore W., "Modern Instrumental Method of Accurately and Directly Measuring the Useful Life of Turbine Oils," OilDoc Conference and Exhibition, Bv.DE, Feb. 1-3, 2011.
Selby, Theodore W., and Miiller, Gregory C., U.S. Appl. No. 61/795,088, filed Oct. 10, 2012 entitled, "Oil Life Measurement."
Tannas Company, Tannas Quantum (TM) Oxidation Tester, www.tannasco.com . . . , 2 pages plus downloaded brochure and Declaration of Conformity, printed Mar. 3, 2011.
Wikipedia, "Luer Taper," Nov. 1, 2011 10:16, printed Jul. 19, 2012.

*Primary Examiner* — Maureen Wallenhorst
(74) *Attorney, Agent, or Firm* — Christopher John Rudy

(57) ABSTRACT

Rotatable bomb device having a stationary hollow housing and a rotatable component inside the housing provides for very good temperature calibration, temperature recording and, when desired, sample control. The device can have at least one of an insulating lower disc or washer; a plurality of staggered heating bands encompassing a stationary housing; a dry scan port; a rear upper and/or lower port; and an extraction/injection fitting for access to the interior of the stationary housing. The device may be used to react or attempt to react substance(s), for example, generally as in ASTM Method D2272 testing of turbine oil.

20 Claims, 18 Drawing Sheets

Quantum™ Oxidation Test
RPVOT Certification Data
S/N QOT-1206-252

Temperature Profile – Using Calibration Port

| 'Dry' Port Scan | |
|---|---|
| Position from Bottom (inches) | Temperature (°C) Measured |
| 0.0 (Bottom) | 154.9 * |
| 0.5 | 154.7 |
| 1.0 | 154.8 |
| 1.5 | 154.6 |
| 2.0 | 154.3 |

* Critical Calibration Temperature

OIL LIFE MEASUREMENT

This claims the benefit under 35 USC 119(e) of provisional No. U.S. 61/795,088 filed on Oct. 10, 2012 A.D. The specification of that application is incorporated herein by reference in its entirety, which thus includes all of its written descriptions, claims, and drawings.

FIELD OF THE INVENTION

This concerns a rotatable bomb device and method of testing/reacting with the device.

BACKGROUND TO THE INVENTION

The publication of G. H. von Fuchs at al., paper entitled "The Rotary Bomb Oxidation Test for Inhibited Turbine Oils," In the ASTM Bulletin (now the Materials Research and Standards), No. 186, December 1952, pp. 43-46, provided the technical basis for ASTM Method D2272 approved and published in 1964 as a "Rotary Bomb Oxidation Test". This ASTM Method is now termed the "Rotating Pressure Vessel Oxidation Test" (RPVOT). In this test method, ASTM D2272, a 50-gram sample plus a 5-gram amount of water and a high-purity (99.9%) copper coil are placed in a beaker and loaded into a pressure chamber, sealed and then filled with 99.5% pure oxygen gas at a pressure of 620-kPa, and the entire pressurized chamber Is rotated in an oil bath at 150° C. Initially, the end of test (EOT) was considered to be when the oxygen pressure fell rapidly with oil oxidation. This was called the "break point." Later, the EOT was set at a 175-kPa (25.4 PSI) pressure drop, which at the time corresponded with the onset of the break point. With more modern fluids, this has not always been found to be the case, and the break point sometimes comes well after a 175-kPa chamber pressure value is reached. Basically, however, that instrument and technique simulated many hours of oil in service in a turbine, for example, by minutes in the RPVOT. The RPVOT is widely used and provides information on the quality and potential longevity of turbine lubricants in service. However, original equipment for D2272 was not without some difficulties in the practice of the original ASTM D2270 method. For example, the following is noted:

It is difficult to maintain an about 100-liter oil bath at 150° C. to bathe multiple, for example, four, test assemblies (which are often rotated through the bottom of the tank where seals are leak-prone under those operating conditions).

Even more important is the fact that running tests in a liquid bath requires that tests in all of the RPVOT units in the bath must be completed before any of them can be disassembled, cleaned and replaced in the bath for another analysis. This retards oxidation testing significantly.

Operator safety Is a concern, especially to avoid being splashed by very hot oil when the heavy (about 10~15 pounds) pressure-vessel assemblies are loaded or removed after the test.

In addition, the odor and fumes that develop from the bath oil frequently lead to the need for special hoods, associated floor space, and cleaning needs.

Recently, an instrument was developed to ameliorate or eliminate these problems, which simplified the RPVOT procedure and, in addition, was capable of providing considerable new information and versatility: the Quantum® instrument. Compare, U.S. Pat. No. 7,678,328 B1. The Quantum® instrument entirely avoids using bath oil for heating, simplifies sample loading and retrieval, rotates only the sample beaker instead of the whole pressure chamber and reduces test turn-around time since each sample is run in its own Quantum® instrument. Thus, rather than rotating several complete assemblies simultaneously in an oil bath, only the inner test sample beaker is rotated by magnetic coupling at the bottom of the pressure chamber, which remains stationary. A computer is used to record pressure and temperature data from one to four units. See, e.g., FIG. 1. Since the Quantum® instrument is intended to be, in general, an isothermal reactor, first studies focused on the effects on temperature effects of the oxidation reaction going on in the oil sample during the application of the RPVOT technique. Various observations were reported by T. W. Selby et al., "Studies of the Oxidation Dynamics of Turbine Oils—Initial Data from a New Form of the Rotating Pressure Vessel Oxidation Test,". This paper by Selby was given at an ASTM Symposium on Oxidation and Testing of Turbine Oils; 5-8 Dec. 2005, in Norfolk, Va. and published in October 2007 in the Journal of ASTM International.

For the first time, the design of the Quantum instrument—with only the sample rotating—permitted inserting a pressure-sealed temperature sensor into the test fluid during test as shown in FIG. 2. When this was done, the ASTM D2272 RPVOT test method was able to record the test fluid. The temperature recording showed a phenomenon never before seen in this test. At the time at which oxidation began to increase rapidly as shown by a relatively precipitous decrease in the oxygen pressure in the pressure chamber, some oils showed an exotherm in temperature in which the sample temperature would rise as shown in FIG. 3 That the test fluid oxidation rate could produce such a response was an important new finding. It provided a way of contrasting oxidation inhibitors and the oxidation response of test oils. The degree of temperature increase was found to range from a few tenths of a degree to well over +15° C., in cases perhaps to +30° C. or so, and this information on the variation of oxidation reactivity is, in itself, informative about inhibitors.

Difficulties with previous endeavors in the field include that repeatability, accuracy and precision are not as good as one would hope in order to obtain the best data so necessary for a more complete understanding of the sample under test. This, in turn, can lead to less in the way of advancement, for example, in the world of lubricants, than would allow with better data. It would be desirable to improve upon the art as well as to provide the art an alternative.

DISCLOSURE OF THE INVENTION

Provided is a rotatable bomb device such as disclosed in U.S. Pat. No. 7,678,328 B1, modified hereby to provide for very good temperature calibration, temperature recording and, when desired, sample control. A method of using the device, for example, generally as in ASTM Method D2272 testing of turbine oil, say, ASTM D2272-09, is also provided. Further, not only extraction but also insertion of an additive, reactant and/or a catalyst can be effected under seal of the rotatable bomb device, especially when provided with a reaction lid with tubular support system, which can employ a Luer-Lok® syringe or equivalent to gain the effect.

The invention is useful in testing and reacting fluids and so forth.

Significantly, by the invention, the art is advanced in kind. Even better temperature and/or sample control is/are efficiently provided in a rotatable bomb device, to an unmatched level, which can engender dramatic increases in the exposition, quality and/or quantity of fluid test data. As well, less energy is employed with present embodiments when conducting testing than with prior devices. Also, not only extraction but also insertion of additives, reactants and/or catalysts can be accomplished, now with very high accuracy and precision, not to forget increased durability, from the present reaction lid with tubular support system, notably increasing versatility of the device. Any of a number of suitable fluids can be tested or operated upon, say, oleaginous liquids, for example, turbine oils, engine oils, transmission fluids, and so forth and the like.

Numerous further advantages attend the invention.

The drawings form part of the specification hereof. With respect to the drawings, which are not necessarily drawn to scale, the following is briefly noted:

Figure 20:
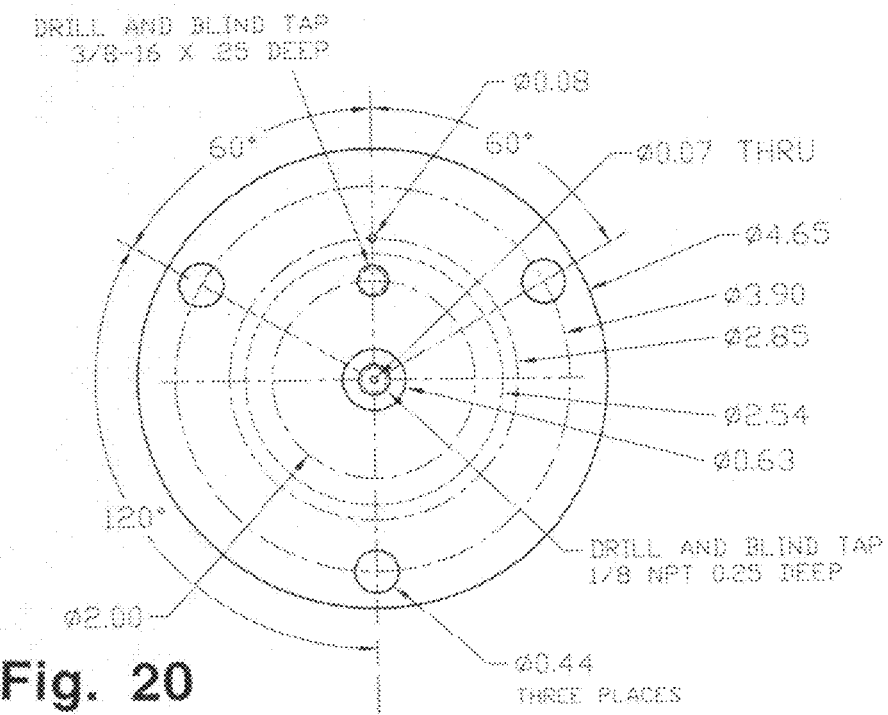
Figure 21:
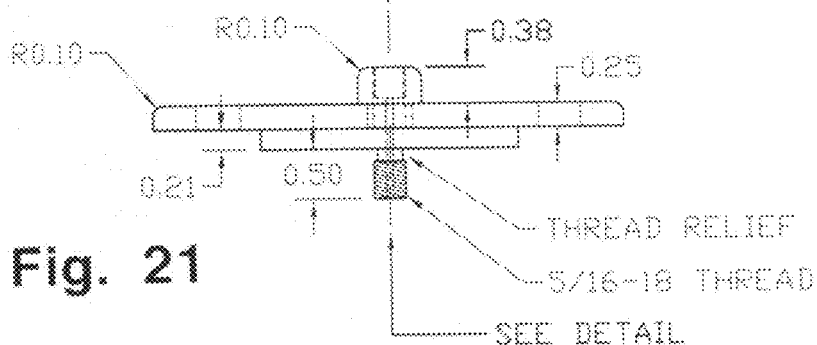
Figure 22:
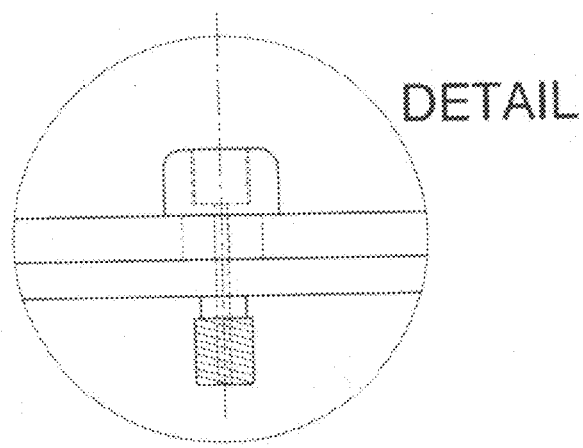

FIGS. 20-22 depict a reaction lid for a device hereof, with FIG. 20 a top plan view of the lid, FIG. 21 a side plan view of the lid, and FIG. 22 a detailed side plan view of part of the lid. Unless otherwise noted, dimensions, listed in inches, have tolerances as follows: 0.0, ±0.015; 0.00, ±0.010; and 0.000±0.005; angles are +1°; and surface finish is #62. The depicted reaction lid is made of #304 stainless steel; the inside surface is diamond knurled; a #12 finish is present top and bottom; and all edges are deburred and broken.

Figure 23:
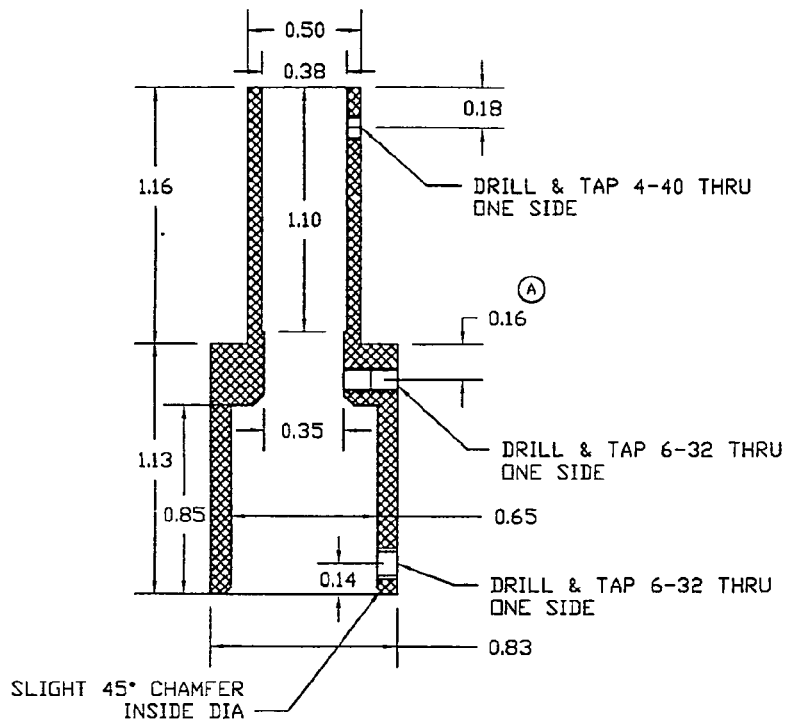
Figure 24:
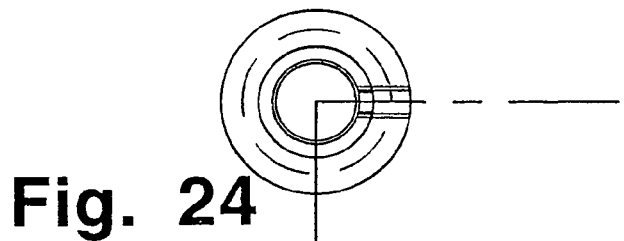
Figure 25:
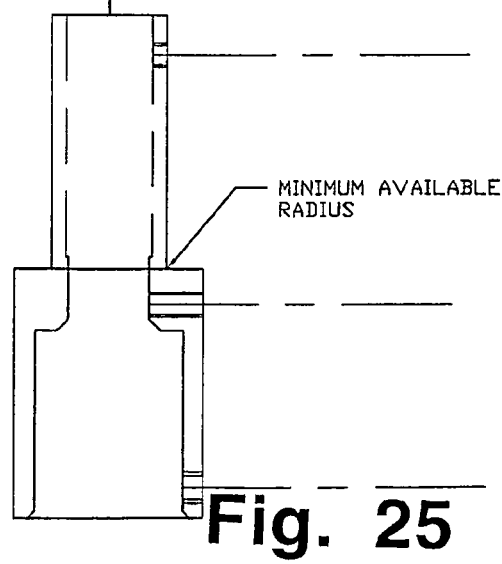

FIGS. 23-25 depict a tubular extraction support, which is for use with the reaction lid of FIGS. 20-22, with FIG. 23 a side sectional view of the tubular extraction support, FIG. 24 a side plan view of the tubular extraction support, and FIG. 25 a top plan view of the tubular extraction support. Unless otherwise noted, dimensions, listed in inches, have tolerances as follows: 0.0, ±0.015; 0.00, ±0.010; and 0.000±0.005; angles are ±1°; and surface finish is #62. The depicted tubular extraction support is made of #304 stainless steel; and all edges are deburred and broken.

Figure 26:
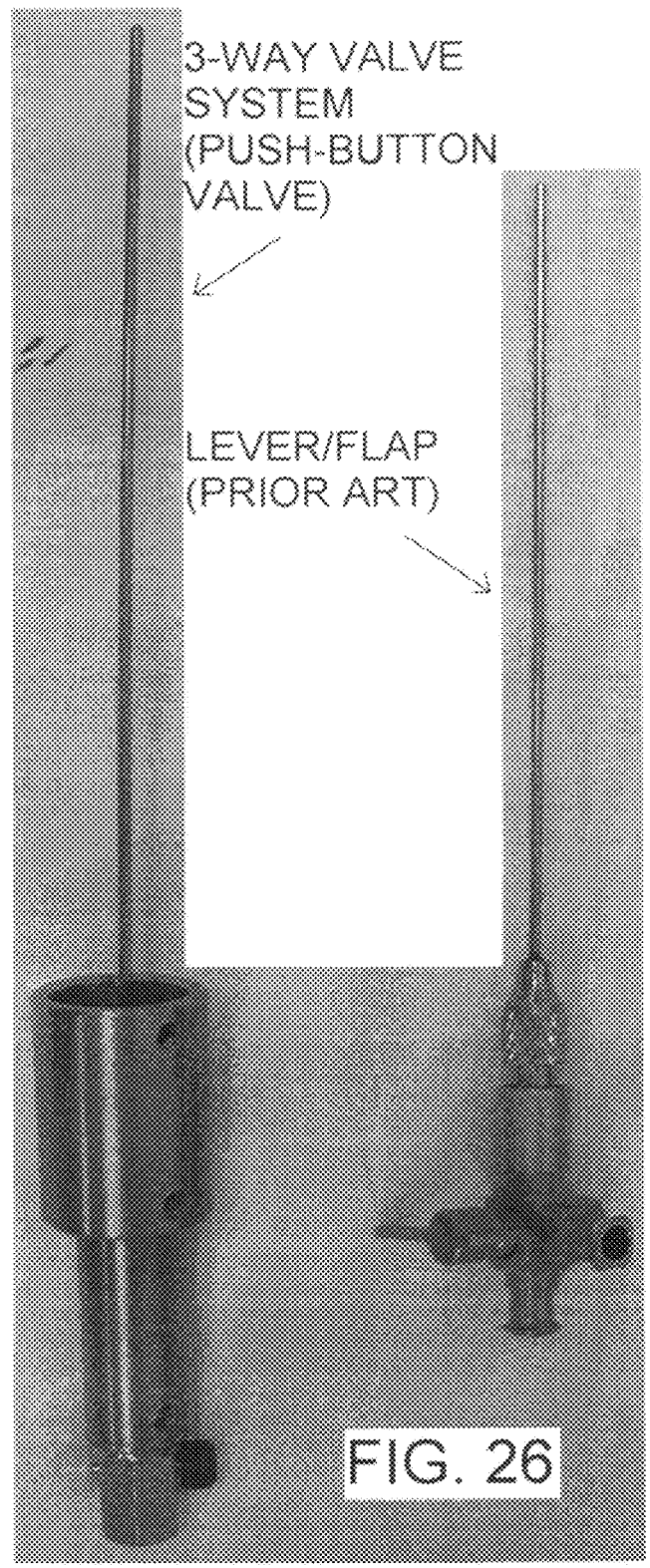

FIG. 26 is a side by side view of lever (prior art) and present extraction/insertion systems.

Figure 27A:
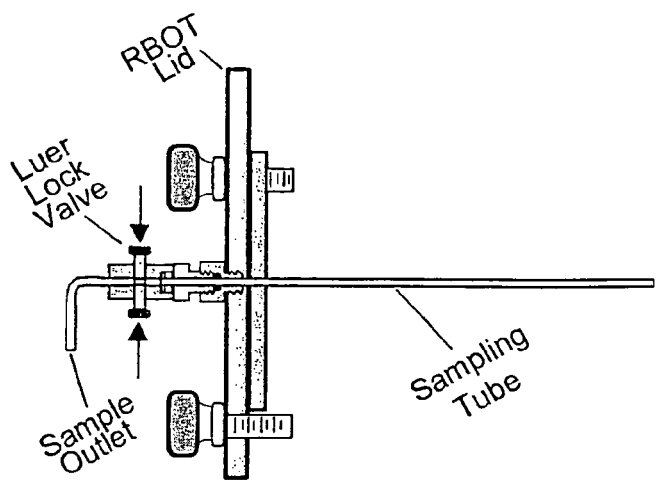
Figure 27B:
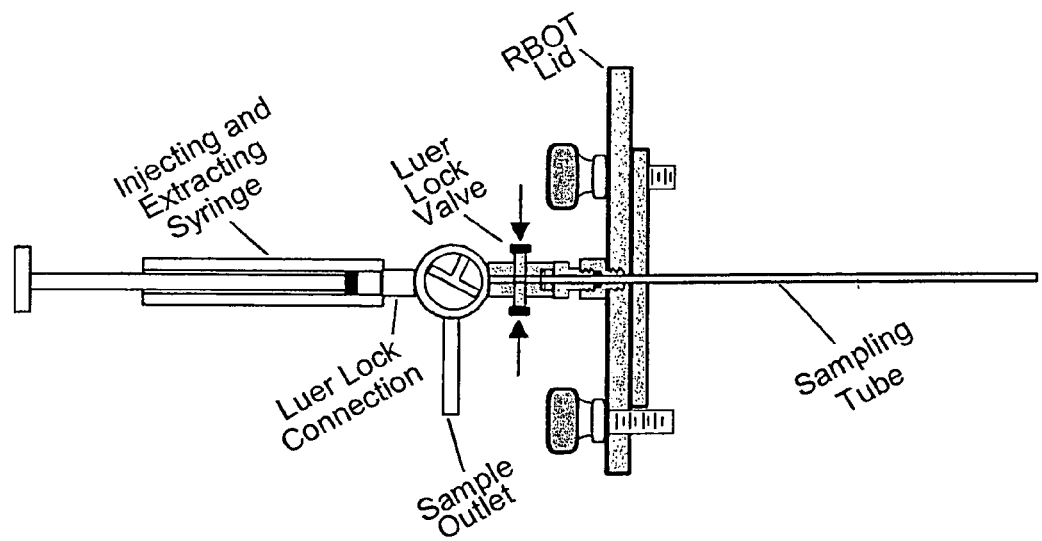

FIGS. 27A and 27B show a reaction lid such as of FIGS. 20-22, which may be found in combination with the tubular support system of FIGS. 23-25 (not illustrated here), having a simple sample outlet (FIG. 27A) or a three-way valve and Luer-Lok® syringe or equivalent (FIG. 27B).

Figure 28:
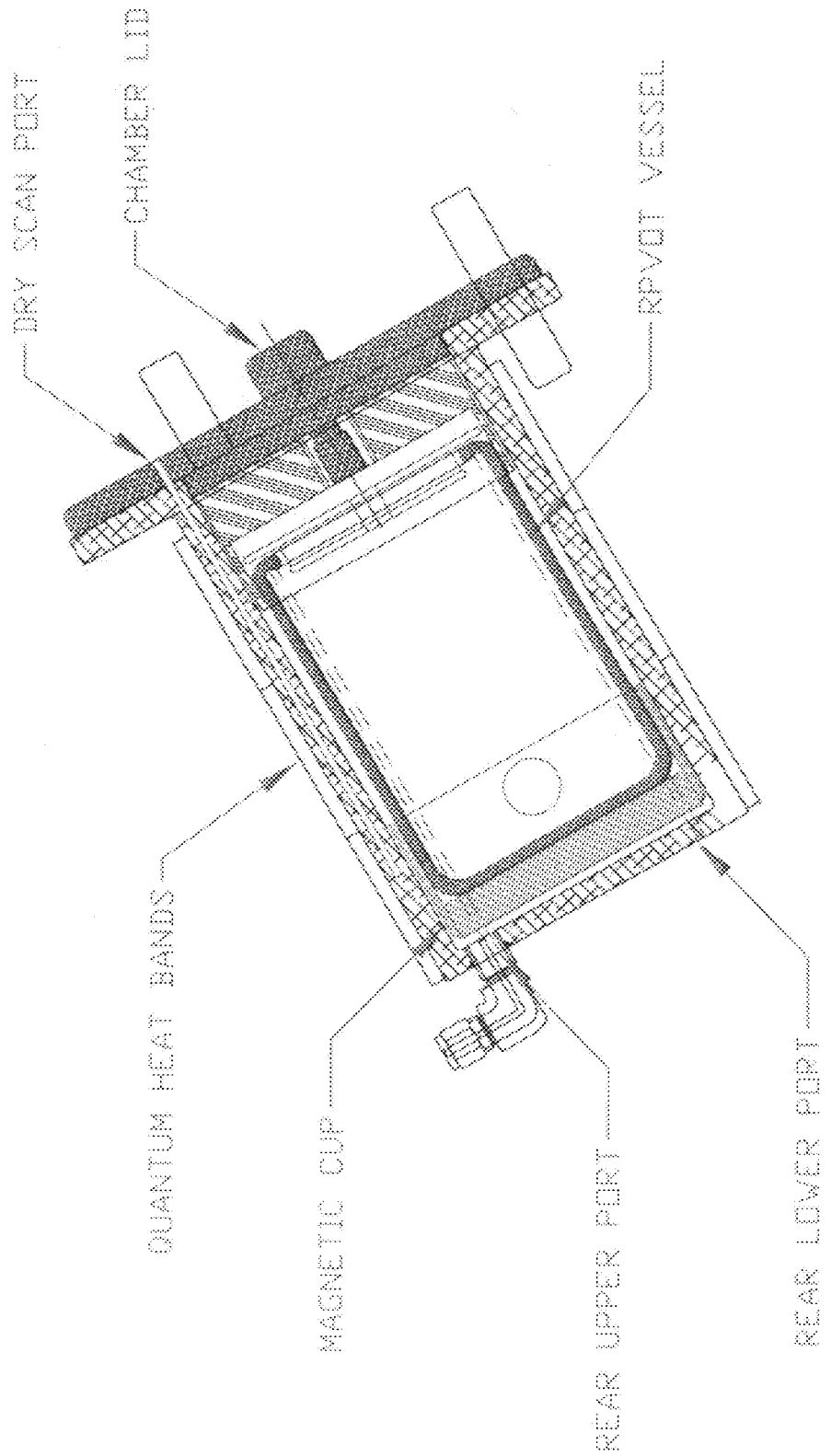
Figure 29:
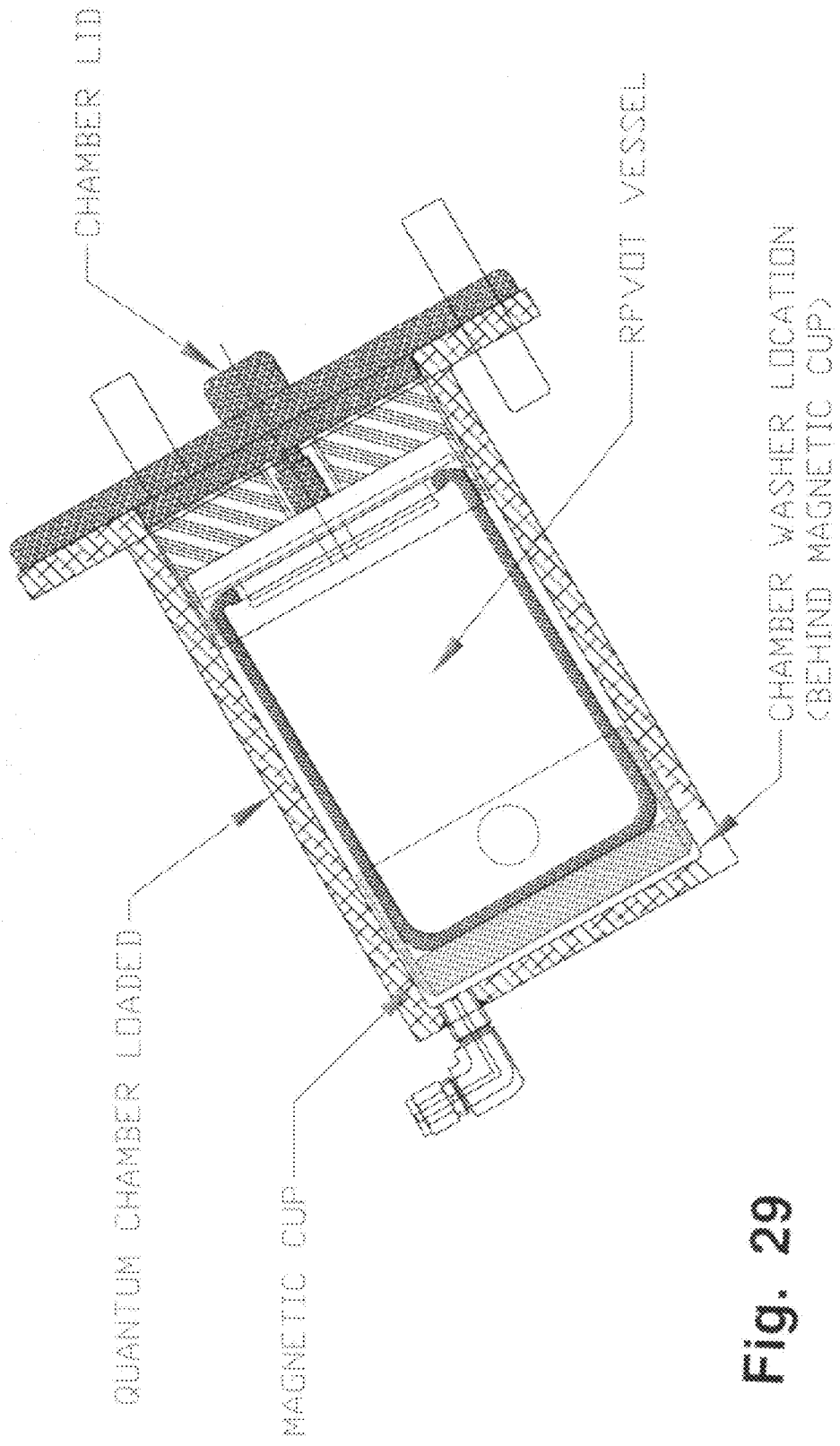

FIGS. 28 and 29 are side plan views of reaction chambers of embodiments hereof.

Figure 30:
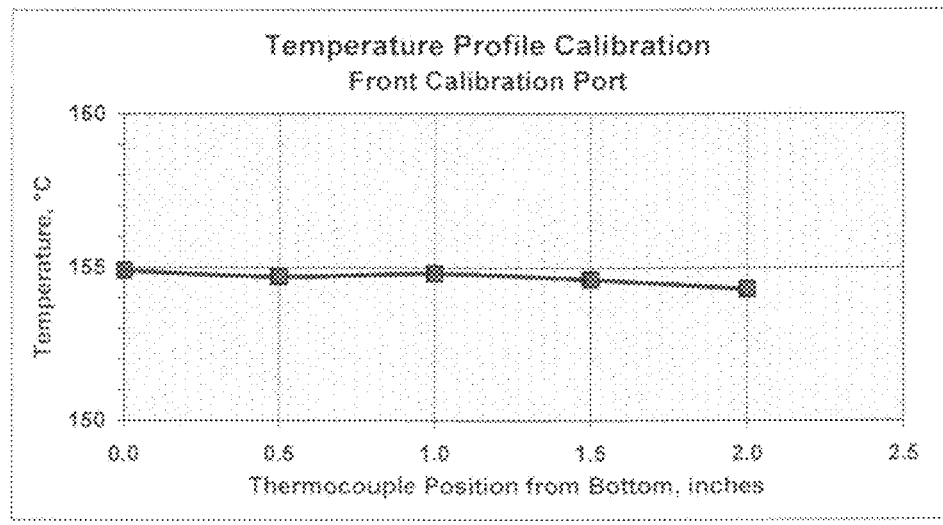

FIG. 30 is a view of temperature profile calibration using a dry port.

The invention can be further understood by the detail set forth below, which may be read in view of the drawings. The same is to be taken in an illustrative and not necessarily limiting sense.

A key feature of the present rotatable bomb device in addition to an insulating chamber upper washer (FIG. 3) is an insulating chamber lower disc (FIGS. 4A and 4B) that can be employed on the inside bottom of the pressure chamber to provide for the excelling control of temperature so beneficial during testing by blocking energy lost at the bottom of the chamber particularly in conjunction with auxiliary temperature-control feature(s). The lower disc can be employed in place of poly ether ether ketone (PEEK) feet at the bottom of the magnetic cup that would provide an air gap for insulating heat loss and reduce bottom friction. The auxiliary temperature-control feature(s) can embrace any of a number of measures, to include, for instance, providing a fan to reduce temperature fluctuation of the pressure chamber by drawing air through the housing of the device and thus to maintain a steady flow of tempering air over band heaters encircling the stationary pressure chamber of the device. Of the band heaters, say, one or two, can be operated continuously at the lower level at a reduced energy, pulsed electrical flow, which can heat up reactants quickly and keep them heated; while the remaining band heaters are automatically controlled to adjust the pressure chamber contents of gas and sample to the desired test temperature. Thus, a more reliable and/or rapid reaction response can be provided for more controlled rate of oxidation of the sample. And so, even with use of less energy, oxidation induction times for data collection can be made more reliable and informative. Plus, an extraction/and injection fitting can provide for sampling or introduction of substances during testing. And, as depicted in FIG. 4C, multiple heating bands, for example, three, are staggered with their termini not lined up so that a "cold spot" does not develop on one side of the chamber; and an overheat control, formerly on the central of a three-band arrangement, is now on the upper band, or even on two heating bands, say, upper and lower bands.

The following example further illustrates the invention.

EXAMPLE 1

Figure 1:
FIG. 1 (prior art) is a view of a set of Quantum® units with an associated computer.
Figure 2:
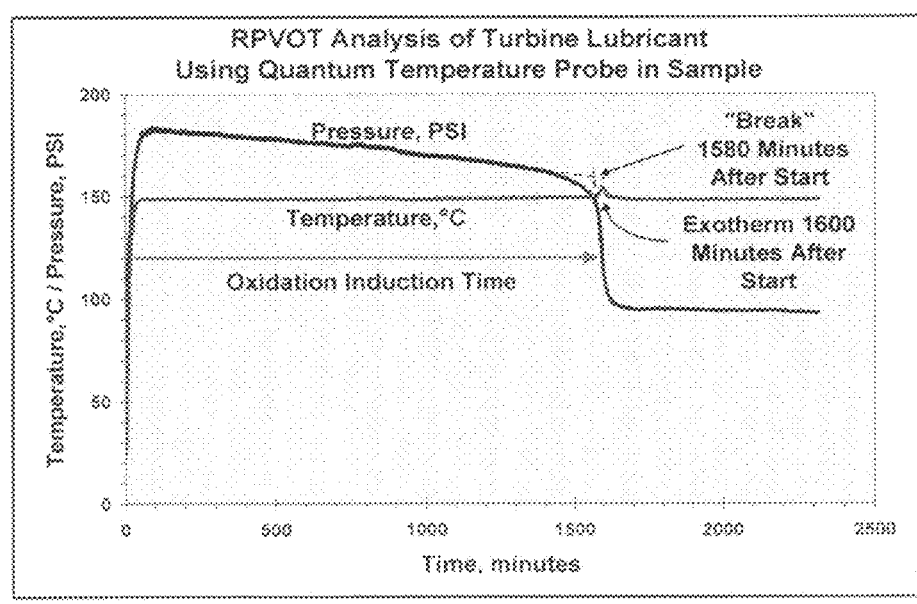
FIG. 2 (prior art) is a graph of results from a reference oil.
Figure 3:
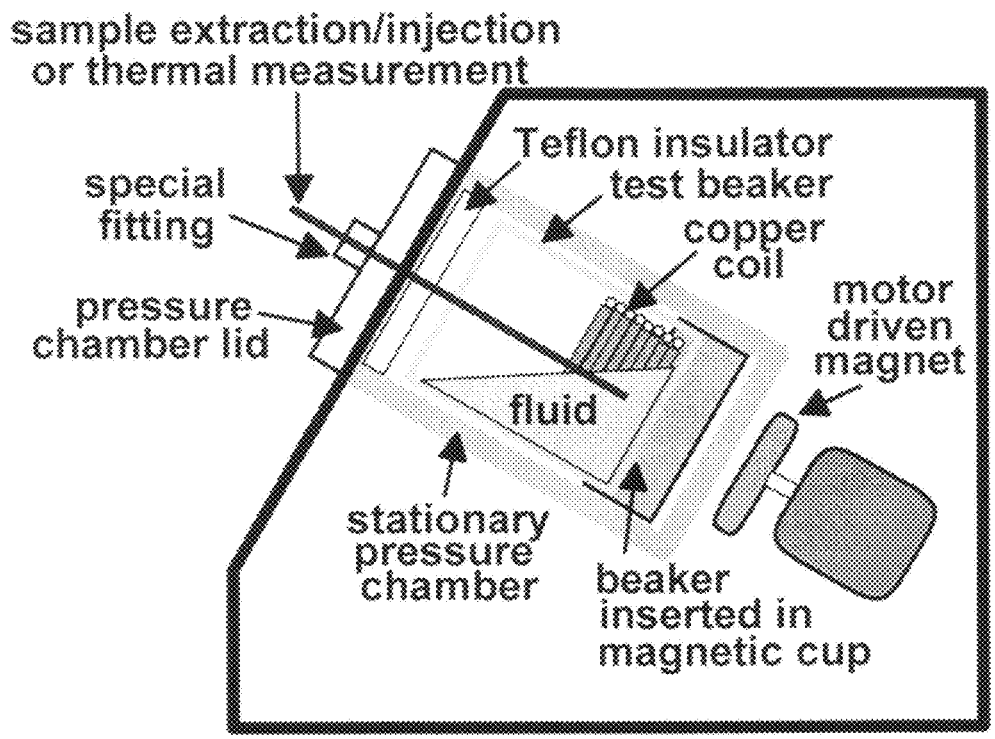
FIG. 3 is a side plan view of a rotatable bomb hereof.
Figure 4A:
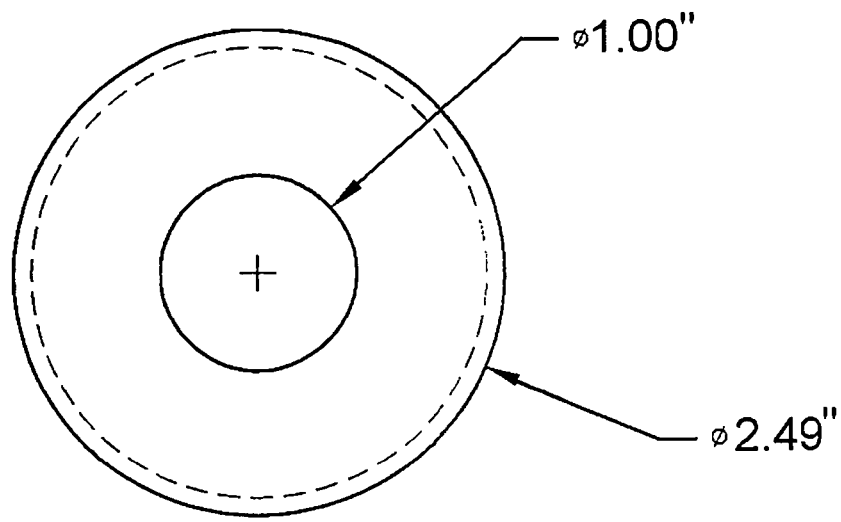
FIG. 4A is a front plan view and FIG. 4B is a side plan view of a Teflon® polytetrafluoroethylene chamber washer, which can be employed as a disc on the inside bottom of the pressure chamber such as of the rotatable bomb of FIG. 3.
Figure 4B:
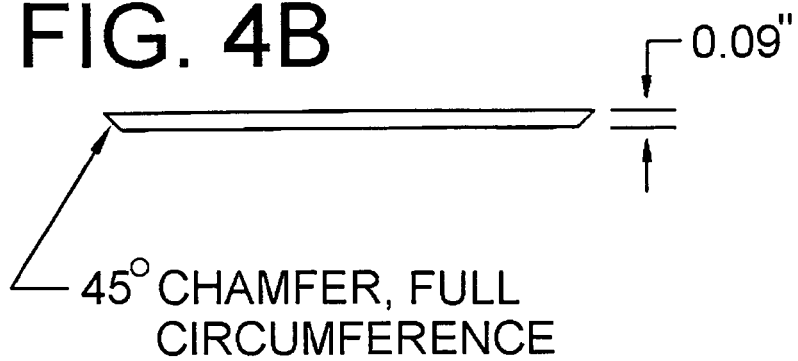
Figure 4C:
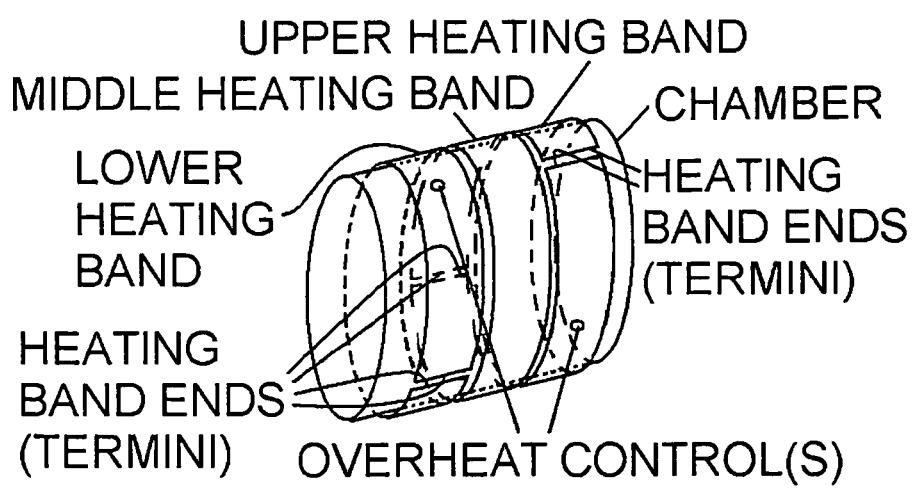
FIG. 4C is a plan view of a reaction cylinder chamber employable in the rotatable bomb of FIG. 3.

A rotatable bomb device otherwise such as depicted in FIG. 1 can be modified with a Teflon® polytetrafluoroethylene insulating chamber washer or disc such as depicted in present FIGS. 3, 4A and 4B. An internal fan can be provided the device and operated throughout testing. An extraction/injection fitting and other features can be provided as seen in FIGS. 3, 5 and 20-29. RPVOT testing can be effected more precisely and reliably therewith.

Figure 5:
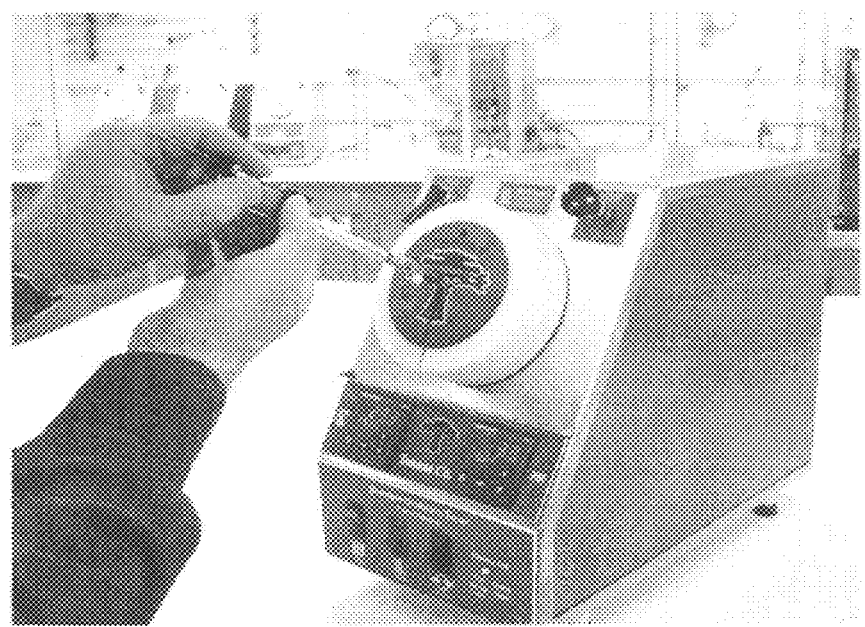
FIG. 5 is a view of extraction or injection of a sample from a rotatable bomb during testing.
Figure 6:
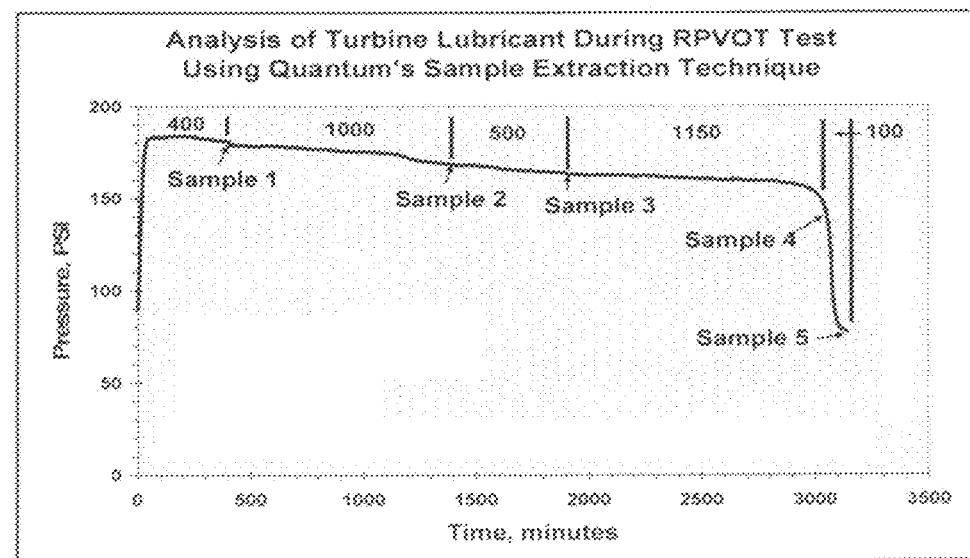
FIGS. 6-19 are graphs of test results from use of a rotatable bomb.

The extraction and injection fitting allows access to the test fluid during testing for the first time. Direct access to the sample is made possible through the front lid of the instrument's pressure chamber. Specifically, a special pressure chamber lid is used that has a fitting permitting extraction of material from the test sample. Similarly, gas or liquid may be injected into the test sample when desired for experimental studies. As seen in FIGS. 3 and 5, access to the sample is had through the fitting—here, a three-way valve on the lid of the pressure chamber, which permits use of a small syringe to collect a portion of the sample being tested. Compare FIGS. 20-29. The pressure chamber is stationary; only the beaker and cup are rotated by magnetic coupling to a variable speed motor outside of the pressure chamber. Extracting small amounts of the sample during test is relatively simple. Injection of a material of interest is also permitted into the test sample thereby. Data obtained in the RPVOT on turbine oil using the extraction system is shown in FIG. 6. Extractions were made at five intervals in the RPVOT test with the device.

Figure 7:
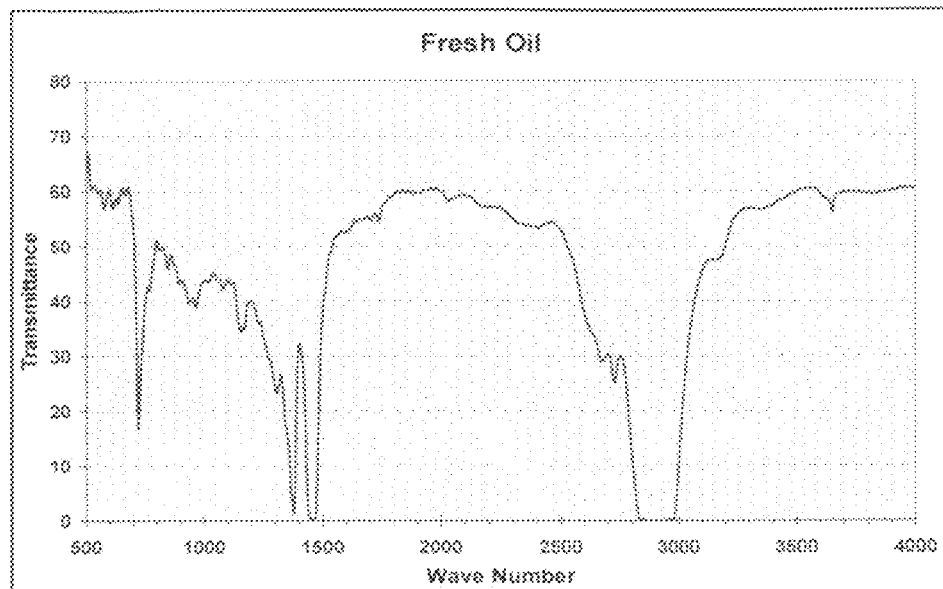

FIG. 7 shows an initial Fourier-transform infrared (FTIR) spectrum of turbine oil before applying the present test technique.

Figure 8:
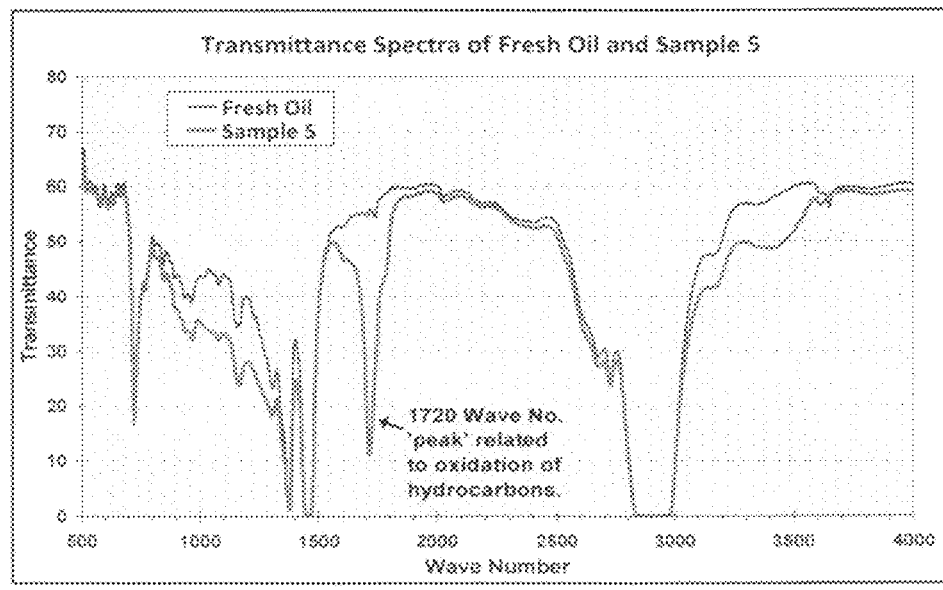

FIG. 8 shows both the spectrum of FIG. 7 and EOT turbine oil FTIR spectra. The oxidation peak' at 1720 cm-1 was chosen for interest. For greater clarity and information, however, subtracted is the FTIR spectrum of the fresh oil from that of each of the small (<0.4 g) samples extracted during testing.

Figure 9:
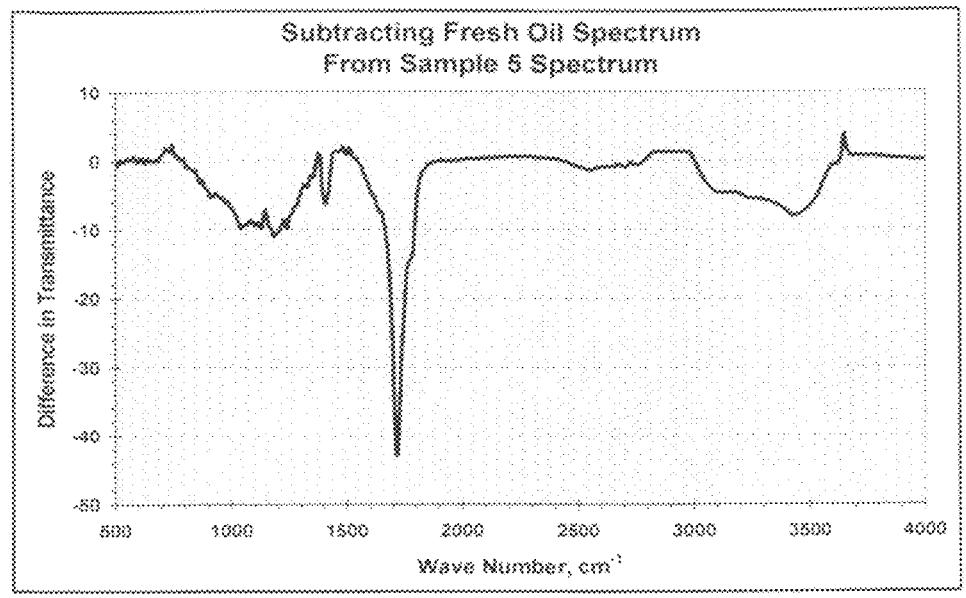

FIG. 9 shows the simplifying benefit of subtracting the FTIR spectrum of the fresh turbine oil from the EOT spectrum. The 'peak' at 1720 Wave Number explicitly shows the effects of RPVOT stress on the oil.

Figure 10:
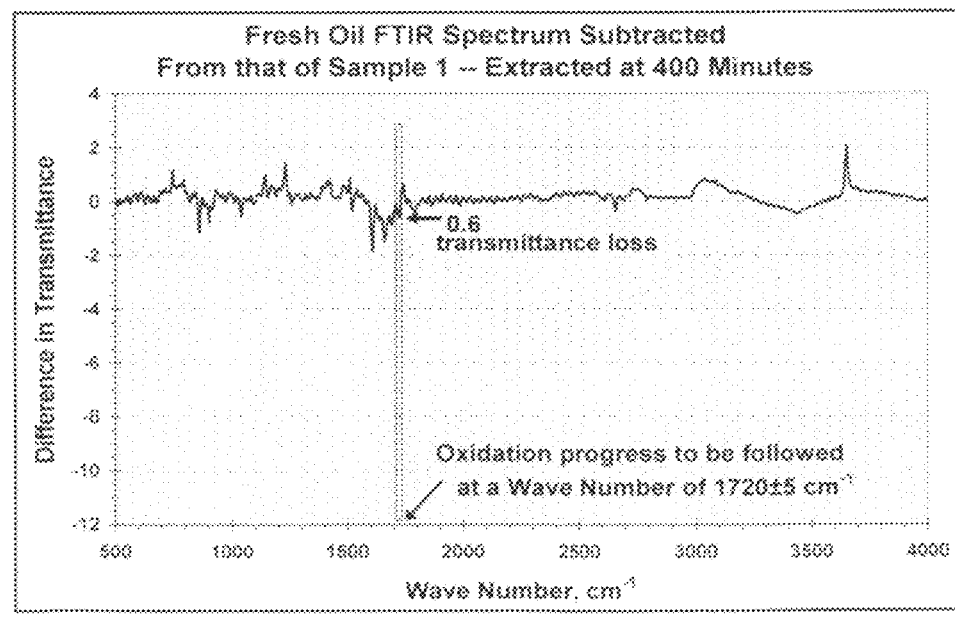
Figure 11:
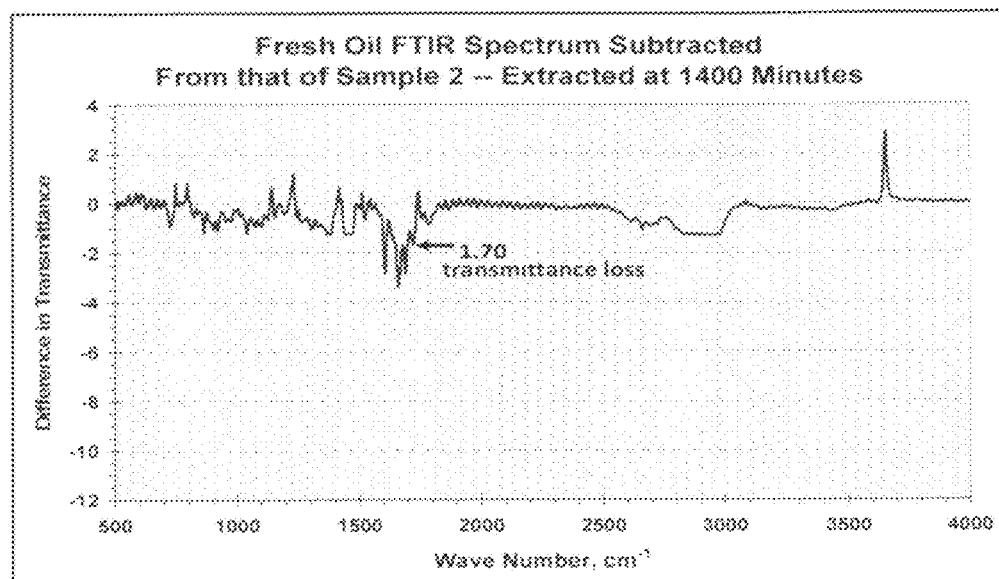
Figure 12:
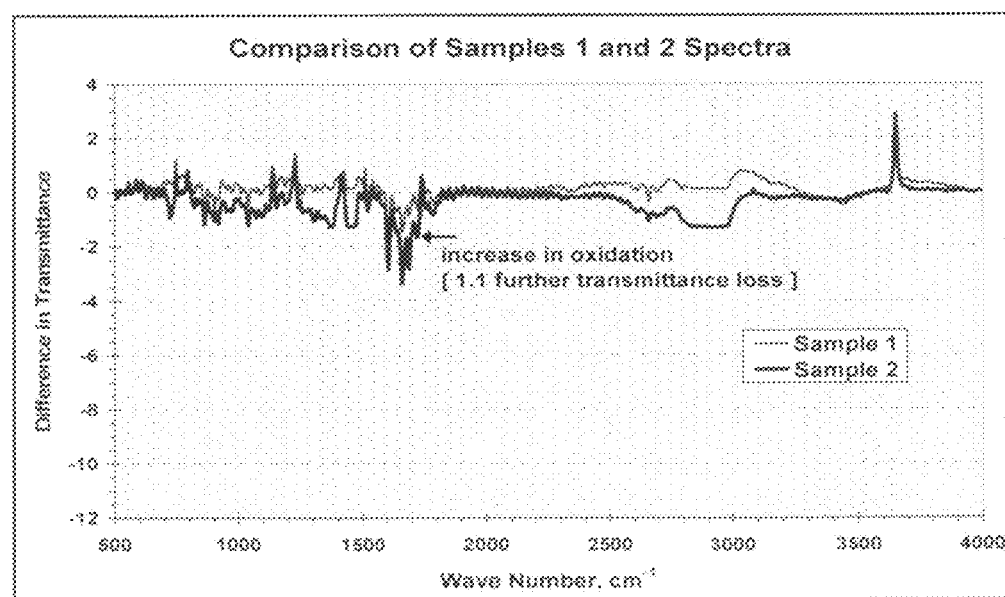

FIG. 10 shows the fresh oil FTIR spectrum subtracted from that of Sample 1 extracted at a 400-minute time. FIG. 11 shows the fresh oil FTIR spectrum subtracted from that of Sample 2 extracted at a 1400-minute time. FIG. 12 shows a comparison of the spectra of Samples 1 and 2.

Figure 13:
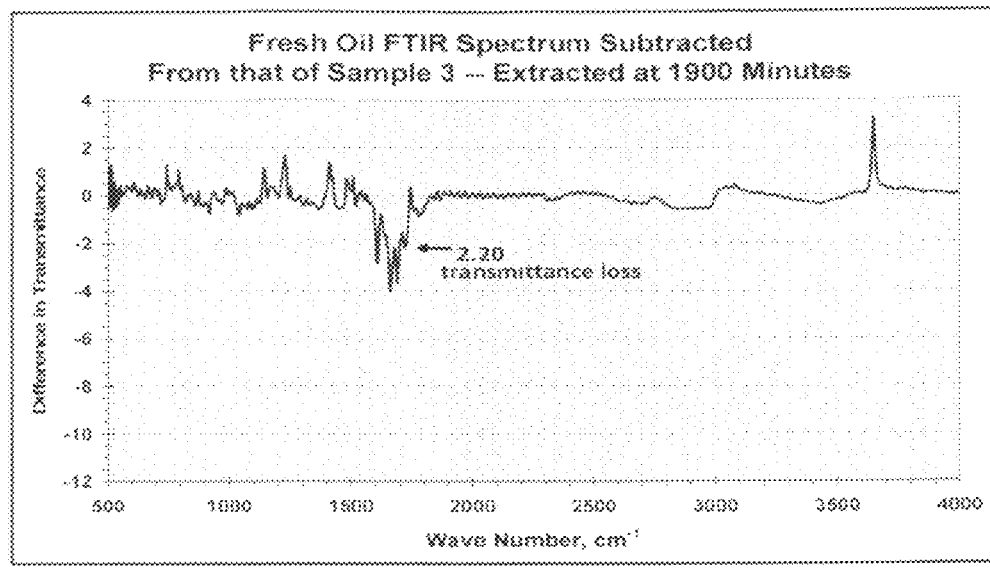
Figure 14:
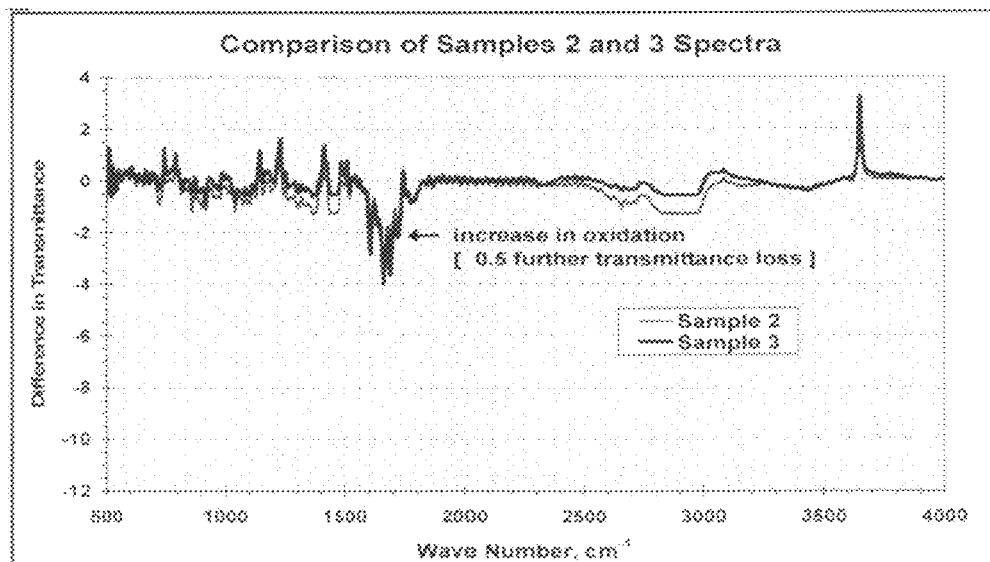

FIG. 13 shows the fresh oil FTIR spectrum subtracted from that of Sample 3 extracted at a 1900-minute time. FIG. 14 shows a comparison of the spectra of Samples 2 and 3.

Figure 15:
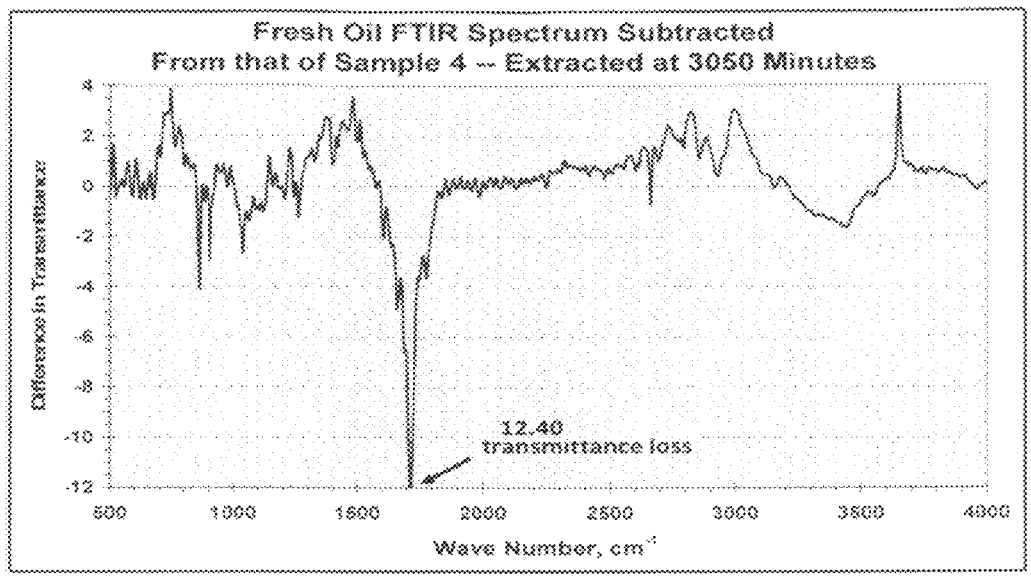
Figure 16:
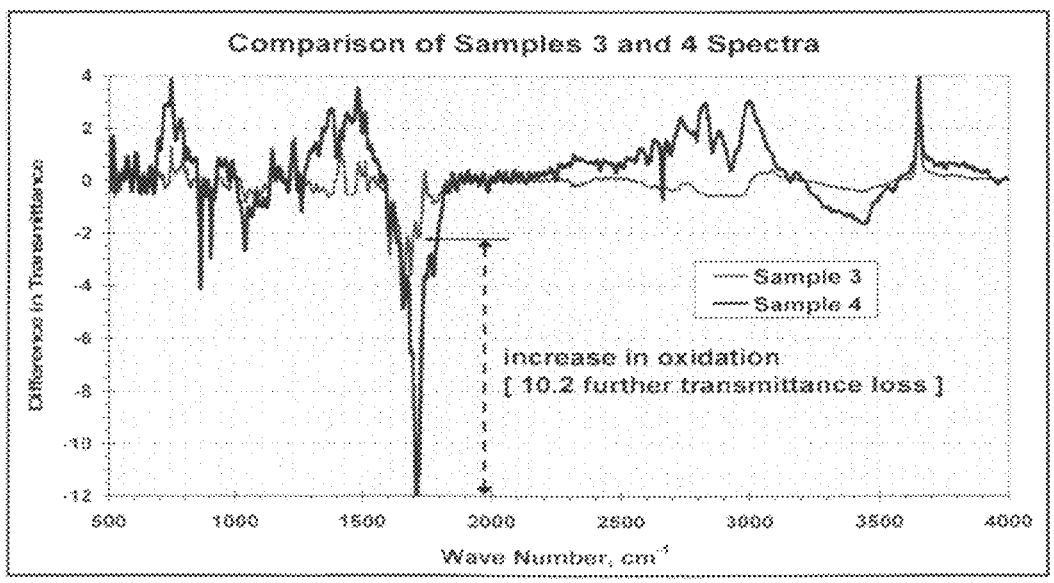

FIG. 15 shows the fresh oil FTIR spectrum subtracted from that of Sample 4 extracted at a 3050-minute time. FIG. 16 shows a comparison of the spectra of samples 3 and 4.

Figure 17:
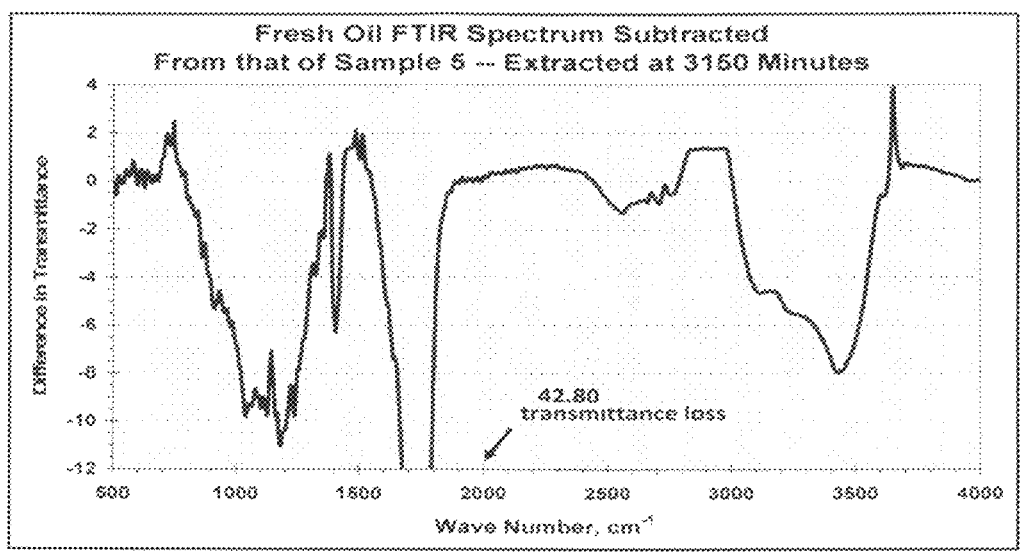
Figure 18:
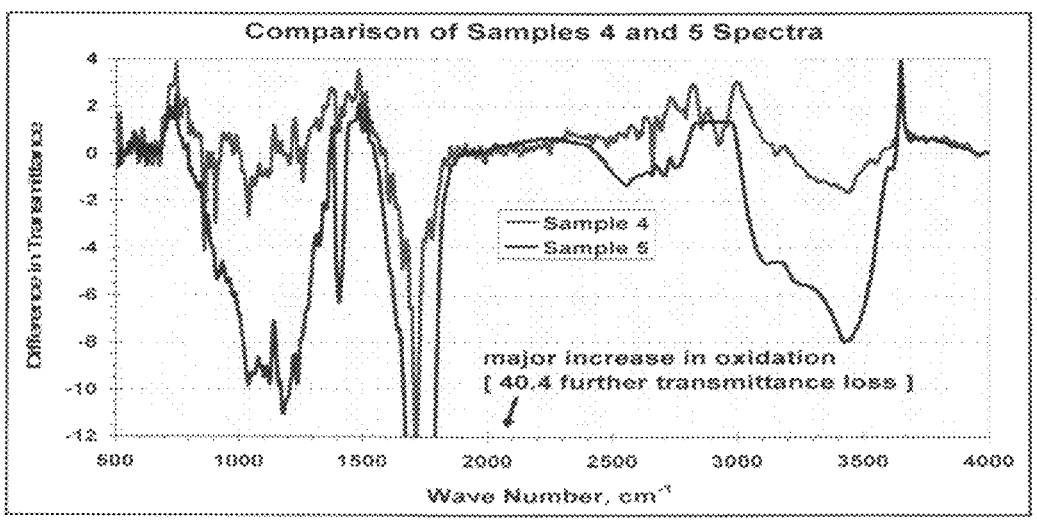
Figure 19:
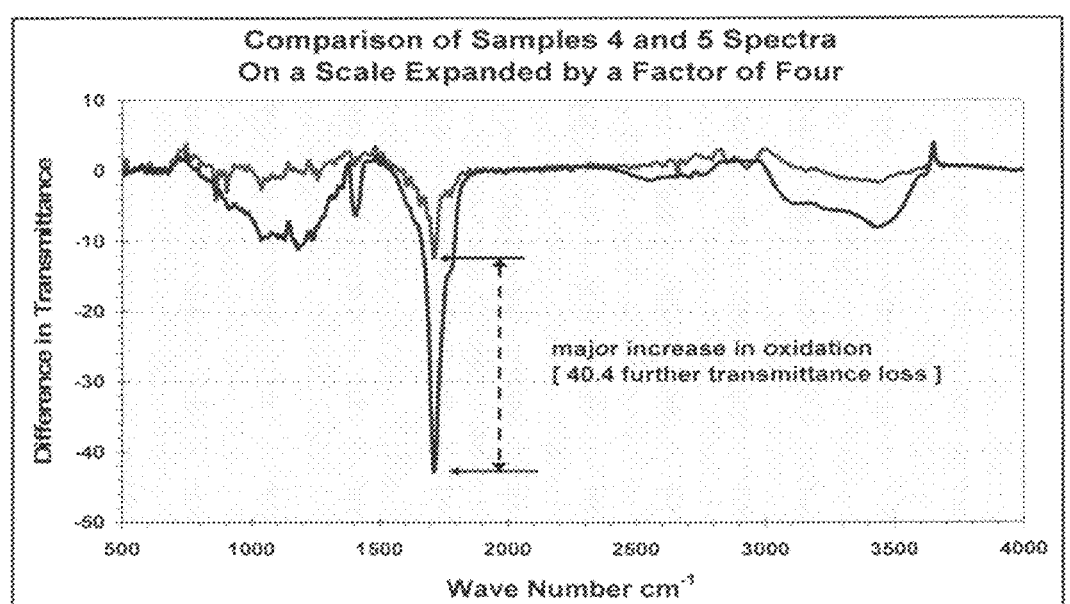

FIG. 17 shows the fresh oil FTIR spectrum subtracted from that of sample 5 extracted at a 3150-minute time, and FIG. 18 shows a comparison of the spectra of samples 4 and 5. FIG. 19 shows a comparison of the spectra of samples 4 and 5, on a scale expanded by a factor of four.

Some observations were made:

Selecting and monitoring the oxidation resistance of turbine oils using the device in the present RPVOT-type testing is important both to the facilities using such oils and for those providing such products and their additives. However, there is much more to be learned by studying the detailed process of oxidation and the progressive changes that occur in additives and base oils composing turbine oils. While one Wave Number was followed herein to determine oxidation, many other portions of the spectra may be followed so as to generate an important understanding of antioxidant degradation; observe the mechanics of sludge formation; determine chemistry of the formation of the precursors of varnish; and appraise other important factors affecting turbine oils in use. Similarly, and perhaps of keen interest to turbine operators and additive manufacturers, the injection of materials, for example, antioxidants, into the test fluid has the potential of finding ways of maintaining the turbine oil in use.

The technique of extraction analysis of turbine oil demonstrated hereby also can be advantageously applied to turbine oils taken periodically from an operating turbine itself or from the rotating bomb, or from both. These analyses can demarcate the remaining time until the oil reaches a condition shown by FTIR spectra considered to be unfavorable to the turbine. Such a condition may be related to oxidation, formation of varnish precursors, or other oil decomposition concerns that the turbine operator may have. Such evaluation of the turbine oil taken periodically and analyzed as done hereby can determine the specific rate of oxidative degradation and/or varnish precursor increase in the particular turbine application in which the oil is being employed.

EXAMPLE 2

The rotatable bomb device of Example 1 is fitted with three staggered heating bands with overheat control on the upper of the three. See, FIG. 4C. Heat, temperature and energy control excels. Hence data collection can be more accurate, precise and reliable.

FURTHER DISCLOSURE

Embodiments hereof can include an improved combination for extraction and/or injection of material of interest such as shown by the reaction lid of FIGS. 20-22 and the tubular support system of FIGS. 23-25. Compare, FIG. 26—again, a side by side view of flap/lever (prior art) and three-way valve extraction/insertion systems. See also, FIG. 27B—which, again, is a view of the reaction lid of FIGS. 20-22 plus a Luer-Lok® syringe or equivalent, which may be employed in combination with the tubular support system of FIGS. 23-25.

The improved combination can be employed with improved rotatable bomb device embodiments, for example, as depicted in FIGS. 28 and 29, which also can have a chamber washer such as that of FIGS. 4A-4B located behind the magnetic cup in lieu of PEEK plastic pegs or feet with air insulation so as to improve insulation and temperature control as well as energy efficiency of the device, as well as the staggered heating bands such as depicted in FIG. 4C, typically with the top band "on" all the time and the bottom two bands adjusted to keep the temperature constant within the bomb based on thermocouple readings. Various monitoring ports can be provided such as follows:

Dry scan port: tuning. A thermocouple or temperature sensor can be inserted through this port and slid to any appropriate depth or position to tune or calibrate the the temperature of the bomb at various positions. See, FIG. 30.

Rear upper and lower ports: control of temperature. A thermocouple or temperature sensor can be inserted through each of these ports to monitor temperature during testing or reaction of the bomb. Adjustments may be made manually or electronically.

INCORPORATION BY REFERENCE

U.S. Pat. No. 7,678,328 B1 is incorporated herein by reference in its entirety. This, of course, includes all of its written descriptions, claims, and drawings.

CONCLUSION TO THE INVENTION

The instant invention is thus provided. Various aspect(s), feature(s), part(s), step(s), subcombination(s) and/or combination(s) can be employed with or without reference to other aspect(s), feature(s), part(s), step(s), subcombination(s) and/or combination(s) in the practice of the invention, and numerous and sundry adaptations and modifications can be effected within its spirit, the literal claim scope of which is particularly pointed out as follows.

What is claimed is:

1. In a rotatable bomb device including a stationary housing with a hollow interior for receipt of a rotatable component to a vessel, with support for the rotatable component in the interior, and including, in the housing, the rotatable component, in which the rotatable component is or includes an inner container that will be rotated by magnetic interaction of a magnet which is coupled to the rotatable component or the inner container and a rotating magnet driver outside the hollow interior, the improvement which comprises provision in the rotatable bomb device of at least one of the members (A, B, C, D, E, F) of the group consisting of:

A. an insulating lower disc or washer located inside, bottom of the stationary housing, which provides for additional control of temperature by blocking energy that otherwise would be lost at the bottom of the stationary housing from the rotatable component, and which can be employed in lieu of pegs or feet on the bottom of the rotatable component that would provide an air gap for insulating heat loss and reduce bottom friction;

B. a plurality of staggered heating bands encompassing the stationary housing, each of which able to be controlled or turned off independently of the other(s);

C. a dry scan port in the stationary housing, accessible from outside the housing, front, into which a thermocouple or temperature sensor can be inserted and slid to any appropriate depth or position to tune or calibrate temperature;

D. a rear upper port in the stationary housing, accessible from outside the housing, rear, into which a thermocouple or temperature sensor can be inserted and slid to any appropriate depth or position to monitor temperature during use of the bomb;

E. a rear lower port in the stationary housing, accessible from outside the housing, rear, into which a thermocouple or temperature sensor can be inserted and slid to any appropriate depth or position to monitor temperature during use of the bomb;

F. an extraction/injection fitting for access to the interior of the stationary housing through a lid thereto, which includes a tubular support system and a three-way valve and locking syringe system for employment therewith.

2. The improvement of claim 1, wherein the interior of the housing and exterior of the rotatable component are generally cylindrical.

3. The improvement of claim 2, which includes at least one of the members A and B.

4. The improvement of claim 3, which includes the member F.

5. The improvement of claim 2, which includes the member F.

6. The improvement of claim 1, which includes at least one of the members A and B.

7. The improvement of claim 6, which includes the member F.

8. The improvement of claim 1, which includes the member F.

9. A method of attempting to react or reacting substance(s), which comprises providing a rotatable bomb device in which is included a stationary housing with a hollow interior for receipt of a rotatable component to a vessel, with support for the rotatable component in the interior, and including, in the housing, the rotatable component, in which the rotatable component is or includes an inner container that will be rotated by magnetic interaction of a magnet which is coupled to the rotatable component or the inner container and a rotating magnet driver outside the hollow interior, the improvement which comprises provision in the rotatable bomb device of at least one of the members (A, B, C, D, E, F) of the group consisting of:

A. an insulating lower disc or washer located inside, bottom of the stationary housing, which provides for additional control of temperature by blocking energy that otherwise would be lost at the bottom of the stationary housing from the rotatable component, and which can be employed in lieu of pegs or feet on the bottom of the rotatable component that would provide an air gap for insulating heat loss and reduce bottom friction;

B. a plurality of staggered heating bands encompassing the stationary housing, each of which able to be controlled or turned off independently of the other(s);

C. a dry scan port in the stationary housing, accessible from outside the housing, front, into which a thermocouple or temperature sensor can be inserted and slid to any appropriate depth or position to tune or calibrate temperature;

D. a rear upper port in the stationary housing, accessible from outside the housing, rear, into which a thermocouple or temperature sensor can be inserted and slid to any appropriate depth or position to monitor temperature during use of the bomb;

E. a rear lower port in the stationary housing, accessible from outside the housing, rear, into which a thermocouple or temperature sensor can be inserted and slid to any appropriate depth or position to monitor temperature during use of the bomb;

F. an extraction/injection fitting for access to the interior of the stationary housing through a lid thereto, which includes a tubular support system and a three-way valve and locking syringe system for employment therewith; providing the substance(s) to the rotatable component/inner container; and, under bomb conditions, attempting to react or reacting the substance(s) in the rotatable component/inner container by operating the rotatable bomb device including rotation of the rotatable component/inner container.

10. The method of claim 9, wherein the rotatable bomb device includes the member A, wherein the disc or washer is made of polytetrafluoroethylene; the member B, wherein the plurality of staggered heating bands is made up of three bands encircling the housing in a substantially abutting, side-by-side relationship; the member C; the member D; the member E; and the member F.

11. The method of claim 9, which is a test of turbine oil as the substance(s) generally as in which a 50-gram sample of the turbine oil plus a 5-gram amount of water and a high purity copper coil are placed in the rotatable component/inner container and loaded into the hollow interior, sealed and then filled with a pure oxygen gas at a pressure of 620 kPa, and the rotatable component/inner container is rotated at 150° until an end of test (EOT), wherein the EOT is at least one of the following:

a "break point," where oxygen pressure falls with oxidation of the turbine oil; and a 175-kPa pressure value is reached.

12. In a rotatable bomb device including a stationary housing with a hollow interior for receipt of a rotatable component to a vessel, with support for the rotatable component in the interior, and including, in the housing, the rotatable component, in which the rotatable component is or includes an inner container that will be rotated by magnetic interaction of a magnet which is coupled to the rotatable component or the inner container and a rotating magnet driver outside the hollow interior, the improvement which comprises provision in the rotatable bomb device of at least one of the members (A, B, C, D, E, F) of the group consisting of:

A. an insulating lower disc or washer located inside, bottom of the stationary housing, which provides for additional control of temperature by blocking energy that otherwise would be lost at the bottom of the stationary housing from the rotatable component, and which can be employed in lieu of pegs or feet on the bottom of the rotatable component that would provide an air gap for insulating heat loss and reduce bottom friction;

B. a plurality of staggered heating bands encompassing the stationary housing, each of which able to be controlled or turned off independently of the other(s);

C. a dry scan port in the stationary housing, accessible from outside the housing, front, into which a thermocouple or temperature sensor can be inserted and slid to any appropriate depth or position to tune or calibrate temperature;

D. a rear upper port in the stationary housing, accessible from outside the housing, rear, into which a thermocouple or temperature sensor can be inserted and slid to any appropriate depth or position to monitor temperature during use of the bomb;

E. a rear lower port in the stationary housing, accessible from outside the housing, rear, into which a thermocouple or temperature sensor can be inserted and slid to any appropriate depth or position to monitor temperature during use of the bomb;

F. an extraction/injection fitting for access to the interior of the stationary housing through a lid thereto, which includes a tubular support system and a three-way valve and locking syringe system for employment therewith;

provided that the improvement includes at least one of the members C, D and E.

13. The improvement of claim 12, wherein the interior of the housing and exterior of the rotatable component are generally cylindrical.

14. The improvement of claim 13, which includes at least one of the members A and B.

15. The improvement of claim 14, which includes the member F.

16. The improvement of claim 13, which includes the member F.

17. The improvement of claim 13, which includes the member A, wherein the disc or washer is made of polytetrafluoroethylene; the member B, wherein the plurality of staggered heating bands is made up of three bands encircling the housing in a substantially abutting, side-by-side relationship; the member C; the member D; the member E; and the member F.

18. The improvement of claim 12, which includes at least one of the members A and B.

19. The improvement of claim 18, which includes the member F.

20. The improvement of claim 12, which includes the member F.

* * * * *